United States Patent [19]

Leston

[11] Patent Number: 4,480,140
[45] Date of Patent: Oct. 30, 1984

[54] PROCESS FOR ALKYLATING PHENOLIC COMPOUNDS TO PRODUCE ORTHO OR PARA-MONOALKYLATED OR 2,4- OR 2,6-DIALKYLATED PHENOLS

[75] Inventor: Gerd Leston, Pittsburgh, Pa.

[73] Assignee: Koppers Company, Inc., Pittsburgh, Pa.

[21] Appl. No.: 475,719

[22] Filed: Mar. 16, 1983

[51] Int. Cl.$^3$ .................. C07C 37/00; C07C 39/06
[52] U.S. Cl. ........................... 568/784; 568/780; 568/782; 568/774; 568/779; 568/799; 564/396; 564/442
[58] Field of Search ............... 568/780, 782, 784, 774, 568/779, 799; 564/396, 442

[56] References Cited

U.S. PATENT DOCUMENTS

| | | | |
|---|---|---|---|
| 2,194,215 | 3/1940 | Brunson | 568/780 |
| 2,452,154 | 10/1948 | Ross | 568/779 |
| 2,494,993 | 6/1950 | Foster | 568/779 |
| 2,842,595 | 7/1958 | Rigternik | 568/780 |
| 3,413,347 | 11/1968 | Worrel | 568/780 |
| 3,592,951 | 7/1971 | Zaweski | 568/784 |
| 3,726,882 | 4/1973 | Traise et al. | 568/780 |
| 3,946,086 | 3/1976 | Gershanov et al. | 568/780 |
| 4,072,724 | 2/1978 | Parker | 568/784 |
| 4,122,287 | 10/1978 | Zakharove et al. | 568/784 |
| 4,215,229 | 7/1980 | Greco | 568/784 |
| 4,309,407 | 12/1981 | Meltsner et al. | 568/784 |

OTHER PUBLICATIONS

Brinson et al., "J. Amer. Chem. Soc.", vol. 63, pp. 270–272, (1941).
Carltin et al., "J. Amer. Chem. Soc.", vol. 72, pp. 2762–2763, (1950).
Caldwell et al., "J. Amer. Chem. Soc.", vol. 61, pp. 2354–2357, (1939).

Primary Examiner—Werren B. Lone
Attorney, Agent, or Firm—Daniel J. Long; Herbert J. Zeh, Jr.

[57] ABSTRACT

Phenols alkylated in the ortho and/or para positions are produced in good yields and in the absence of isomers from phenolic compounds having at least two alkylateable ortho-ortho or ortho-para positions open. The phenolic compound is first partially chlorinated or brominated and the desired halogenated phenol having at least one open position ortho or para is reacted with an aldehyde having one to four carbon atoms and a secondary non-aromatic amine. The reaction is conducted in the liquid phase with a stoichiometric amount of the phenolic compound and stoichiometric or excess of stoichiometric amounts of the aldehyde and the amine. The reaction is performed at a temperature of from about 0° C. to about 100° C. to produce an aminoalkylated halogenated phenolic compound. This aminoalkylated halogenated phenolic compound is contacted with hydrogen in the presence of a metal catalyst at a temperature of about 100° C. to about 175° C. and at a hydrogen pressure of less than 500 psig to produce the desired phenol having at least one alkyl group ortho or para and at least one open position ortho or para.

38 Claims, No Drawings

PROCESS FOR ALKYLATING PHENOLIC COMPOUNDS TO PRODUCE ORTHO OR PARA-MONOALKYLATED OR 2,4- OR 2,6-DIALKYLATED PHENOLS

BACKGROUND OF THE INVENTION

1. Field of the Invention

The present invention relates to processes for producing alkylated phenols and, more particularly, it relates to processes for alkylating phenols that have at least two replaceable hydrogen in the ortho-ortho or ortho-para positions.

2. Description of the Prior Art

Phenols that are alkylated in the ortho-ortho or ortho-para positions have numerous industrial uses. 2,6-xylenol, for example, is useful as the starting material for various polymers and 2,4-xylenol is the starting material for certain antioxidants. 2,3,6-trimethylphenol is the starting material for Vitamin E.

The method of alkylating phenols that have an open ortho- or para-position with an aldehyde and secondary amine to form an alkyl aminoalkylphenol that is then cleaved by hydrogenolysis to produce alkylated phenols is well known in the art. An example is U.S. Pat. No. 2,194,215 (Bruson et al.) which teaches the methylation of phenolic compounds by condensing the phenolic compounds with at least one molecular equivalent each of formaldehyde and a strongly basic, non-aromatic secondary amine to form phenolic tertiary amines. The phenolic tertiary amine obtained is then subjected to hydrogenolysis, whereby the secondary amine is reformed and a new methylated phenolic compound is produced. The hydrogenolysis is performed in the presence of the hydrogenation catalyst, copper chromite, at a temperature above 100° C. and below 300° C., and preferably between 150° C. and 200° C. By this process phenol can be converted into ortho-cresol, para-cresol, 2,4-xylenol, 2,6-xylenol or 2,4,6-trimethylphenol or mixtures thereof, depending upon whether one, two or three moles each of formaldehyde and a secondary amine are employed for the condensation.

The above described reaction will yield one product in good yield when the aldehyde and the amine are used in excess over the available ortho and para hydrogen as is shown by Bruson and McMullen [J. Am. Chem. Soc. 63, 270, (1941)]. However, when fewer than all the available ortho and para hydrogens are to be replaced, the reaction yields a mixture of mono-, di- and trialkylated phenols as well as positional isomers. Thus, Carlin and Landerl [J. Am. Chem Soc. 72, 2762 (1950)] made 2,6-xylenol from o-cresol rather than from phenol and still obtained less that 50 percent of the desired Mannich base, 2-methyl-6-dimethylaminomethylphenol. Similarly, Caldwell and Thompson [J. Am. Chem. Soc. 61, 756 (1939)] obtained the 2-aminomethylated 3,5xylenol from 3,5-xylenol in less than a 40 percent yield. These authors also opined [J. Am. Chem. Soc. 61, 2354 (1939)] that there was no clear-cut way of getting a good yield of the desired alkylated product. N. P. Greco (U.S. Pat. No. 4,215,229) found that predominantly monoalkylated phenols could be made from parent phenols containing more than one replaceable hydrogen. He also showed, however, that isomers are obtained in nearly equal amounts, and that some dialkylated derivatives are also obtained.

One way of overcoming some of the difficulties attending the prior art is the prior conversion of a phenol having more than one replaceable hydrogen atom to an alkyl derivative having only one replaceable atom. The desired alkyl group is then introduced with an aldehyde and an amine and the resultant Mannich base is converted to the final desired product by hydrogenolysis. Such a process is exemplified by the teachings of Gershanov et al. (U.S. Pat. No. 3,946,086). The above disclosure, however, does not teach how an alkylated phenol may be produced in a good yield and high purity from a phenolic compound having more available ortho or para positions than the number of alkyl groups to be introduced. It is, therefore, an object of the present invention to provide such a process.

SUMMARY OF THE INVENTION

The present invention comprises a process for making a selectively and isomerically pure monoalkylated or dialkylated phenol in a good yield and of a high purity from phenolic compounds containing more open ortho and para positions than those that are to be substituted by the alkyl groups. Pursuant to this invention a phenolic compound having at least two replaceable hydrogen atoms in the ortho-para positions is chlorinated or brominated to produce a halogenated derivative still containing at least one replaceable hydrogen atom. The desired halogenated phenol may then be separated from the unreacted starting phenol, isomeric halogenated phenols and/or under- or overhalogenated phenols by any conventional separation process. The isolated desired halogenated phenol is then reacted with at least stoichometric amounts of an aldehyde of one to four carbon atoms and of a secondary amine to form an aminomethylated halogenated phenol in which all the ortho and para positions are substituted. The condensation of the halogenated phenol with aldehyde and amine occurs in the liquid phase at a temperature in the range of about $-10°$ to $100°$ C. The aminomethylated, halogenated phenol is contacted with hydrogen at a pressure of 50–500 psig and at a temperature of about $100°$ C. to about $200°$ C., preferably in a glass-lined vessel and in the presence of a catalyst preferably containing palladium, platinum, indium, rhodium or rubidium to produce the desired phenol having an alkyl group or two alkyl groups in the position formerly occupied by the corresponding amino-alkyl group or groups and having a hydrogen or two hydrogens in the positions formerly occupied by the halogen atoms. The amine may be obtained from the phenolic compound during the hydrogenolysis and may be in the forms of the hydrohalide salt since a hydrogen halide is formed during the simultaneous removal of the halogen or halogens. The amine may be freed from the halide salt for recycling. It is a further feature of the present invention that undesirable isomers of the haolgenated phenols produced in the first step of the reaction may be reintroduced into the third step of the process, the hydrogenolysis, to convert the undesirable halogenated phenols back to the starting phenol for recyling.

DETAILED DESCRIPTION OF THE INVENTION

The phenolic compounds that are useful in the process of the present invention are those that contain at least two replaceable hydrogen atoms in the ortho and/or para positions to the hydroxyl groups as expressed by the following formulas:

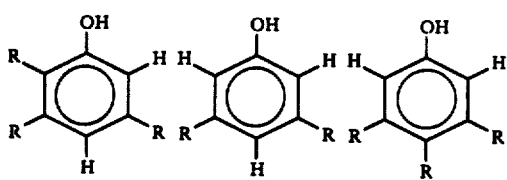

wherein each R independently represents a monovalent substituent such as a hydrogen atom, an alkyl group containing one to six carbon atoms, an aryl group or an aralkyl group. Specific examples of the phenolic compound used in the process of the present invention include phenol, o-cresol, p-cresol, m-cresol, 2,3-xylenol, 2,5-xylenol, phenols having substituents thereon one or more alkyl group such as ethyl, propyl, isopropyl, butyl, amyl, hexyl and cyclohexyl. Also included are phenols having aryl and/or aralkyl groups. Furthermore, included are fused ring phenols such as naphtols and similar compounds, as well as polyhydric phenols exemplified by resorcinol, pyrogallol and hydroquinone. The halogenating compounds of the present invention are the halogens such as chlorine, bromine and iodine, bromine chloride, iodine monochloride, sulfuryl chloride, sulfuryl bromide and the like.

The alkylating compounds of the present invention are aldehydes having one to four carbon atoms. Examples of the aldehydes include formaldehyde in aqueous form or in polymeric form, acetaldehyde, propionaldehyde, isopropionaldehyde, n-butyraldehyde, isobutyraldehyde, sec-butyraldehyde, tert-butyraldehyde. The preferred aldehyde for use in the present invention is formaldehyde.

The secondary amine used in the process of this invention must have sufficient basicity to form the aminoalkylphenol upon reaction with the phenolic compound and the aldehyde. Non-limiting examples of secondary amines which may be used include: diethylamine, dimethylamine, diisopropylamine, diisobutylamine, piperidine, dibutylamine, C-alkylated piperidines, morpholine, C-alkylated morpholines, piperazines, and C-alkylated piperazines. The use of a readily available secondary amine such as dimethylamine, diethylamine, diisopropylamine and piperidine is particularly recommended.

The hydrogenation catalyst used in the process of the present invention in the hydrogenolysis step, wherein the aminoalkylphenol is cleaved into alkylphenol and the secondary amine, contains the commonly used hydrogenation catalysts such as nickel and copper chromite. However, when an amino-alkyl group is ortho to the phenolic hydroxyl group, noble metal catalysts are selected from the group consisting of iridium, palladium, platinum, rhodium and rubidium and mixtures thereof. The metallic components may or may not be deposited on a support, but are generally deposited on an inorganic oxide base or carrier material. Suitable carrier materials are silica aluminas, the crystalline aluminosilicates, alumina, porous or nonporous carbon blacks of small or large specific surface areas, and other carbonaceous materials such as activated carbons, coke, or charcoal and other supporting material like thoria, or kieselguhr. Commercial activated carbons which may be used are available under the trade names of NORIT, NUCHAR and DARCO, but other similar carbon materials familiar to those skilled in the art may be used. The hydrogenolysis catalyst may be prepared by any conventional method, when used without a support and when used with a support; it may be prepared by any conventional method for impregnating a porous carrier with a metallic component. One such manner is to make a composite of the metal component with the catalyst base by forming an aqueous solution of the halide of the metal such as platinum chloride, palladium chloride, etc., further diluting the solution and adding the resultant diluted solution to the base in a steam dryer. Other suitable metal solutions may be employed such as colloidal solutions or suspensions, including the desirable metal cyanides, metal hydroxides, metal oxides, and metal sulfides, etc. In cases where these solutions are not soluble in water at temperatures used, other suitable solvents such as alcohols, ethers, etc. may be utilized.

In the process of this invention, the reactions involved are the following:

(1) Halogenation of the phenol and separation of halogenated phenols

The halogenation is performed in conventional forms by any reagent and under conditions of time, temperature and solvent taught in the prior art. The only parameter dictated by the present invention is the amount of halogen introduced into the phenolic nucleus. Thus, if the phenol has all three ortho para positions open and the final alkylated phenol is to be a phenol dialkylated in these positions, it is desirable to maximize the introduction of only one halogen into the nucleus. Conversely, if the final alkylated phenol is to be a phenol monoalkylated in one of these positions, it is desirable to maximize the introduction of two halogens in the nucleus. In the case of a phenol which has only two replaceable hydrogens in the ortho and/or para positions, it is desirable to maximize the introduction of one halogen. The separation of the products of the halogenation of the starting phenols may be carried out by any of the conventional means such as fractional distillation, steam distillation or crystallization. In some instances, especially where steric or electronic influences direct the haolgen reaction to yield predominantly the desired product, separation may not be necessary.

(2) Aminomethylation of the halogenated phenol

The haolgenated phenolic compound is mixed with the secondary amine and the aldehyde is added to this mixture, and these compounds are reacted to produce the aminoalkylated halogenated phenol. This reaction can take place in any vessel known to those skilled in the art for conducting chemical reactions. The suitable mole ratio of the phenolic compound, secondary amine, and aldehyde fed to the reaction vessel is such that the aldehyde and secondary amine are in excess of stoichiometric quantities and the phenolic compound is in stoichiometric quantity. Thus, if only one position is to be aminoalkylated, it is preferred to use one mole of the halogenated phenol and at least one mole each of the aldehyde and the secondary amine to maximize formation of the desired aminoalkylated halogenated phenol. If the two positions are to be aminoalkylated, it is preferred to use one mole of the halogenated phenol and at least two moles each of the aldehyde and the secondary amine to maximize formation of the desired diaminoalkylated halogenated phenol.

(3) Simultaneous hydrogenolysis of amino group and halogen

After the water is stripped from the solution or after a sufficient amount of methanol is added to make the mixture of water and aminoalkylated halogenated phenol and unreacted reactants a homogeneous mixture and act as a solvent, in order to prevent the water from adversely affecting the catalyst, the aminoalkylated halogenated phenol is then subjected to hydrogenolysis by contacting the aminoalkylated halogenated phenol with hydrogen. The contacting occurs at a hydrogen pressure no higher than about 500 psig and at a temperature in the range of about 120° C. to about 200° C. in the presence of a hydrogenation catalyst. In the case wherein the aminoalkyl group is ortho to the phenolic hydroxyl group it is desirable to use a noble metal catalyst selected from iridium, palladium, platinum, rhodium, or rubidium, or mixtures thereof. The hydrogenolysis is preferably carried out in a glass-lined vessel to prevent any metals other than the type present in the catalyst from contacting the reactants, especially where the aminoalkyl group is ortho to the phenolic hydroxyl group. The hydrogenolysis cleaves the aminoalkylated halogenated phenol to produce an alkylated non-halogenated phenol. Also produced is the secondary amine used in the reaction with the phenolic compound and the aldehyde. This secondary amine may be in the form of the hydro halide produced by the reaction of hydrogen on the halogen removed from the phenolic nucleus.

(4) Separation of amine from phenol

The amine thus tied up may be freed by a base stronger than the amine and the latter can be recycled to the reaction wherein the phenolic compound, secondary amine and aldehyde are reacted. It may be desirable to convert any secondary amine not so tied up as a salt, to a salt to aid in the separation of the amine from the phenol. Also, the hydrogenolysis catalyst can be removed from the reaction vessel, filtered and recycled for reuse in the reaction vessel for further hydrogenolysis.

It is an additional feature of this invention that the undesirable halogenated phenols produced in the halogenation reaction, as described in Step 1, may be converted back to the stating unchlorinated phenol by hydrogenolysis, thus allowing the recovered phenol to be recycled. It is further possible to perform the dehalogenation of the undesirable halogenated phenols simultaneously with the hydrogenolysis of the desired intermediate aminoalkylated halogenated phenol. When the latter procedure is followed, a separation step such as fractional distillation, steam distillation or crystallization is desirable to separate the final desired alkylated phenol from the recovered starting material.

The amount of catalyst used in the hydrogenolysis step is generally between about 0.001 and about 1 percent of the weight of the amino derivatives employed in the reaction. This quantity of palladium is preferentially between about 0.01 percent by weight of the amino derivatives.

The foregoing process may be carried out as a batch-type, semicontinuous or continuous operation utilizing a fixed or moving bed catalyst system for the aminoalkylation step if a catalyst is used and for the hydrogenolysis step. One embodiment entails the use of a fluidized catalyst zone for a hydrogenolysis step, where, in the vessel, the mixture of aminomethylated phenols is passed countercurrently or co-currently through a moving fluidized bed of the palladium on carbon catalyst. The fluidized catalyst, after use, is filtered from the product mixture and is conducted or recycled to the glass-lined vessel for reuse. After the palladium on carbon catalyst has been used for a period of time, it may require regeneration, which can be performed by any method known to those skilled in the art.

Typical synthesis which may be performed by the present invention include the following:

(a) 2,6-dialkylphenol from phenol
phenol→4-halophenol→2,6-diaminoalkyl-4-halophenol→2,6-dialkylphenol.

(b) 2,4-dialkylphenol from phenol
phenol→2-halophenol→2,4-diaminoalkyl-6-halophenol→2,4-dialkylphenol.

(c) 2-alkylphenol from phenol
phenol→2,4-dihalophenol→2-aminoalkyl-4,6-dihalophenol→2-alkylphenol.

(d) 4-alkyl-m-cresol from m-cresol
m-cresol→6-chloro-m-cresol→4-aminoalkyl-6-chloro-m-cresol→4-alkyl-m-cresol.

(e) 2,4-dialkyl-m-cresol from m-cresol
m-cresol→6-chloro-m-cresol→2,4-diaminoalkyl-6-chloro-m-cresol→2,4-dialkyl-m-cresol.

(f) 2-alkyl-m-cresol from m-cresol
m-cresol→4,6-dichloro-m-cresol→2-aminoalkyl-4,6-dichloro-m-cresol→2-alkyl-m-cresol.

Of particular interest is the conversion of m-cresol to 2,3,6-trimethyl phenol, an intermediate in the synthesis of Vitamin E. As Caldwell and Thompson show, m-cresol can be converted by aminomethylation-hydrogenolysis to 2,5-xylenol. They then convered this phenolic compound to 2,4,5-trimethylphenol rather than to the desired isomer. By practicing the subject invention and isolating 4-chloro-m-cresol for diaminomethylation-hydrogenolysis, the desired 2,3,6-dimethylphenol is obtained. The undesirable isomer obtained in the chlorination of m-cresol, 6-chloro-m-cresol, which boils at a temperature close to that of m-cresol and which is difficult to separate from m-cresol, may be converted back to m-cresol by subjecting it or its admixture with m-cresol to hydrogenolysis, either by themselves or in conjunction with the hydrogenolysis of 2,6-diaminomethyl-4-dichloro-m-cresol. If the latter method is chosen, it is preferable to separate the desired 2,3,6-trimethylphenol from m-cresol. This separation may be readily performed by fractional distillation.

The following example shows the aminomethylation and hydrogenolysis of 4-chloro-m-cresol.

EXAMPLE

A solution of 14.2 g (0.10 mmol) of 4-chloro-m-cresol in 50 ml of methanol was prepared. To this was added 45.1 g (0.25 mmole) of 25% aqueous dimethylamine. Under mechanical agitation 20.25 g (0.25 mmole) of 35% aqueous formaldehyde was added at 23°–28° during 17 minutes. The mixture was then refluxed (78° C.) for two hours. Seventy milliliters of methanol was added for the hydrogenation which was performed in a glass-lined shaking autoclave in the presence of 2.3 g of 5% palladium on carbon at 250 psig during 3.5 hours at 120° C. The product was anlayzed GC with the following results:

| Elution Time (min) | Amount[1] (area percent) | Identity |
|---|---|---|
| 2.9 | 1.1 | Unknown |
| 6.0 | 1.5 | Unknown |
| 8.2 | 2.2 | m-cresol |
| 11.3 | 48.4 | 2,5-xylenol |
| 13.1 | 0.8 | 2,3-xylenol |
| 15.6 | 0.5 | Unknown |

-continued

| Elution Time (min) | Amount[1] (area percent) | Identity |
| --- | --- | --- |
| 18.2 | 45.7 | 2,3,6-trimethylphenol |

[1]On a solvent- and dimethylamine-free basis.

Although the invention has been described with a certain degree of particularity, it is to be understood that the present disclosure has been made only as an example and that the scope of the invention is defined by what is hereafter claimed.

What is claimed is:

1. A process for alkylating a phenolic compound having at least two hydrogens available in the ortho-ortho or ortho-para positions to produce a monoalkylated or dialkylated phenol comprising:
   (a) introducing into the phenolic compound a halogen selected from the group consisting of chlorine and bromine to produce a halogenated phenolic compound having from about six to about twenty two carbon atoms and still containing at least one free hydrogen in the ortho or para position and isolating the halogenated phenolic compound which still has one or two hydrogens at the ortho-para positions;
   (b) reacting the isolated halogenated phenolic compound with a saturated aliphatic aldehyde having one to about four carbon atoms and a secondary amine having two to about eight carbon atoms, wherein the halogenated phenolic compound is in a stoichiometric amount and the amounts of aldehyde and of amine are in stoichiometric or excess of stoichiometric amount and in the liquid phase and at a temperature in the range of about 0° C. to about 100° C. to produce a Mannich base type aminoalkylated halogenated phenol;
   (c) contacting the Mannich base type aminoalkylated halogenated phenol with hydrogen in the presence of a hydrogenation catalyst to produce the desired mono or dialkylated phenol and the secondary amine; and
   (d) separating the secondary amine from the mixture to produce the desired monoalkylated or dialkylated phenol.

2. A process for the synthesis of 2,3,6-trimethylphenol comprising:
   (a) halogenating m-cresol with a halogen selected from the group consisting of chlorine, bromine, sulfuryl chlorine and sulfuryl bromide and separating 4-halo-m-cresol from other halogenated m-cresols;
   (b) reacting the 4-halo-m-cresol with formaldehyde and a secondary amine having two to about eight carbon atoms in the liquid phase at a temperature from about 0° C. to 100° C. to produce 2,6-diaminomethyl-4-halo-m-cresol;
   (c) contacting the Mannich base type 2,6-diaminomethyl-4-halo-m-cresol with hydrogen in the presence of a hydrogenation catalyst to produce one or more phenolic compounds, including the desired 2,3,6-trimethylphenol, and the secondary amine; and
   (d) separating the secondary amine from the mixture to isolate a mixture of phenolic compounds and then isolating 2,3,6-dimethylphenol therefrom.

3. A process for alkylating a halogenated phenolic compound having from about six to about twenty two carbon atoms and having one or two hydrogens at the ortho-para positions comprising:
   (a) reacting the isolated halogenated phenolic compound with a saturated aliphatic aldehyde having one to about four carbon atoms and a secondary amine having two to about eight carbon atoms, wherein the halogenated phenolic compound is in a stoichiometric amount and the amounts of the aldehyde and of amine is in stoichiometric or excess of stoichiometric amount and in the liquid phase and at a temperature in the range of about 0° C. to about 100° C. to produce a Mannich base type aminoalkylated halogenated phenol;
   (b) contacting the Mannich base type aminoalkylated halogenated phenol with hydrogen in the presence of a hydrogenation catalyst to produce the desired mono or dialkylated phenol and the secondary amine; and
   (c) separating the secondary amine from the mixture to produce the desired monoalkylated or dialkylated phenol.

4. A process for the synthesis of 2,3,6-trimethylphenol comprising:
   (a) reacting 4-halo-m-cresol with formaldehyde and a secondary amine having two to about eight carbon atoms in the liquid phase at a temperature from about 0° C. to 100° C. to produce 2,6-diaminomethyl-4-halo-m-cresol;
   (b) contacting the Mannich base type 2,6-diaminomethyl-4-halo-m-cresol with hydrogen in the presence of a hydrogenation catalsyt to produce one or more phenolic compounds, including the desired 2,3,6-trimethylphenol, and the secondary amine; and
   (c) separating the secondary amine from the mixture to isolate a mixture of phenolic compounds and then isolating 2,3,6-dimethylphenol therefrom.

5. The process according to claim 3 wherein the secondary amine used is a secondary aliphatic amine.

6. The process according to claim 3 wherein the secondary amine used is a secondary alicyclic amine.

7. The process according to claim 3 wherein the Mannich base type aminoalkylated halogenated phenol is contacted with hydrogen in a glass-lined vessel.

8. The process according to claim 7 wherein the Mannich base type aminoalkylated halogenated phenol is contacted with hydrogen in the presence of a noble metal catalyst selected from the group consisting of palladium, platinum, rubidium, rhodium, indium, and mixtures thereof.

9. The process according to claim 8 wherein the Mannich base type aminoalkylated phenol is contacted with hydrogen at a pressure of less than 500 psig and at a temperature of about 100° C. to about 175° C.

10. The process according to claim 4 wherein the Mannich base type 2,6-diaminomethyl-4-halo-m-cresol is contacted with hydrogen in a glass-lined vessel.

11. The process according to claim 10 wherein the Mannich base type 2,6-diaminomethyl-4-halo-m-cresol is contacted with hydrogen in the presence of a noble metal catalyst selected from the group consisting of palladium, platinum, rubidium, rhodium, indium and mixtures thereof.

12. The process according to claim 11 wherein the Mannich base type aminoalkylated phenol is contacted with hydrogen at a pressure of less than 500 psig and at a temperature of about 100° C. to about 175° C.

13. The process according to claim 3 wherein the separated amine is recycled to be reacted with the halogenated phenolic compound and the aldehyde.

14. The process according to claim 4 wherein the separated amine is recycled to be reacted with the 4-halo-m-cresol and the aldehyde.

15. The process according to claim 1 wherein the undesirable halogenated phenols are subjected to hydrogenolysis either by themselves or mixed with the starting phenol so as to convert the undesirable halogenated phenols to the unhalogenated starting phenol.

16. The process according to claim 1 wherein the undesirable halogenated phenols either by themselves or mixed with the starting phenol are first combined with the aminoalkylated halogenated phenol and subjected to hydrogenolysis and then separation of starting phenol from the alkylated phenolic product is effected.

17. The process according to claim 8 wherein the noble metal catalysts are supported on materials selected from the group consisting of porous and non-porous carbon blacks and silica.

18. The process according to claim 11 wherein the noble metal catalysts are supported on materials selected from the group consisting of porous and non-porous carbon blacks and silica.

19. The process according to claim 15 wherein the catalyst is filtered from the reaction product and recycled to the hydrogenolysis reaction.

20. The process according to claim 3 wherein the seconary amine is added to the halogenated phenolic compound before the aldehyde is added.

21. The process according to claim 4 wherein the secondary amine is added to the 4-halo-m-cresol before the aldehyde is added.

22. The process according to claim 3 wherein the reacting of the halogenated phenolic compound with the amine and the aldehyde is performed in methanol.

23. The process according to claim 4 wherein the reacting of the 4-halo-m-cresol with the amine and the aldehyde is performed in methanol.

24. The process according to claim 3 wherein the catalyst used for the hydrogenation is a palladium on carbon catalyst.

25. The process according to claim 3 wherein the aldehyde used is a 37 percent aqueous formaldehyde solution.

26. The process according to claim 3 wherein the aldehyde used is paraformaldehyde.

27. The process according to claim 3 wherein the amine is separated from the mixture by contacting the mixture with an acid and then extracting the phenolic compounds with an organic solvent immiscible with water.

28. The process according to claim 3 wherein the separated amine is recycled to the reaction of the halogenated phenolic compound, the amine and the aldehyde.

29. The process according to claim 4 wherein the separated amine is recycled to the reaction of the 4-halo-m-cresol, the amine and the aldehyde.

30. The process according to claim 3 wherein the secondary amine is selected from the group consisting of dimethylamine, diethylamine, piperidine and morpholine.

31. The process according to claim 4 wherein the secondary amine used is a secondary aliphatic amine.

32. The process according to claim 4 wherein the seconary amine used is a secondary alicyclic amine.

33. The process according to claim 16 wherein the catalyst is filtered from the reaction product and recycled to the hydrogenolysis reaction.

34. The process according to claim 4 wherein the catalyst used for the hydrogenation is a palladium on carbon catalyst.

35. The process according to claim 4 wherein the aldehyde used is a 37 percent aqueous formaldehyde solution.

36. The process according to claim 4 wherein the aldehyde used is paraformaldehyde.

37. The process according to claim 4 wherein the amine is separated from the mixture by contacting the mixture with an acid and then extracting the phenolic compounds with an organic solvent immiscible with water.

38. The process according to claim 4 wherein the secondary amine is selected from the group consisting of dimethylamine, diethylamine, piperidine and mopholine.

* * * * *